US00PP16982P3

(12) United States Plant Patent
Lehman

(10) Patent No.: US PP16,982 P3
(45) Date of Patent: Aug. 15, 2006

(54) ***ZOYSIAGRASS* PLANT NAMED 'BM230'**

(50) Latin Name: *Zoysia japonica*
Varietal Denomination: BM230

(76) Inventor: Virginia Lehman, 811 Mountain River Dr., Lebanon, OR (US) 97355

( * ) Notice: Subject to any disclaimer, the term of this patent is extended or adjusted under 35 U.S.C. 154(b) by 89 days.

(21) Appl. No.: 10/736,614

(22) Filed: Dec. 17, 2003

(65) Prior Publication Data

US 2005/0138714 P1 Jun. 23, 2005

(51) Int. Cl.
*A01H 5/00* (2006.01)

(52) U.S. Cl. ..... Plt./390

(58) Field of Classification Search ..... Plt./390
See application file for complete search history.

*Primary Examiner*—Kent Bell
*Assistant Examiner*—Annette H Para

(57) ABSTRACT

An asexually reproduced variety of perennial *zoysiagrass* with a unique combination of morphological characters including medium leaf blade width and low floral production.

2 Drawing Sheets

Latin name of the genus and species of the plant claimed: The present invention relates to the genus and species *Zoysia japonica* (L.) Merr.

Variety denomination: 'BM230'.

BACKGROUND OF THE INVENTION

Field of Invention

The present invention relates to a new and distinct asexually reproduced variety of perennial *zoysiagrass* (*Zoysia japonica* (L.)) Merr.

BRIEF SUMMARY OF THE INVENTION

BACKGROUND OF THE INVENTION

This invention relates to a new and distinct perennial zoysiagrass cultivar identified as 'BM230' *zoysiagrass* (herein referred to as 'BM230'). The inventor, Virginia G. Lehman, discovered 'BM230' under cultivated conditions in a lawn near Parker, Tex. 'BM230' was identified as a distinctly different vegetative patch or segregated clonal plant differing by coarser leaf texture and aggressive spread from the suspected parental varieties 'Meyer' (unpatented) and Chinese common seeded *zoysia*. The inventor asexually reproduced 'BM230' by taking vegetative cuttings of the plant material from the lawn including stolons and rhizomes, cutting the rhizomes and stolons into segments, each with a vegetative bud, and rooted them in potting media near Parker, Tex. For purposes of registration under the "International Convention for the Protection of New Varieties of Plants" (generally known by its French acronym as the UPOV Convention) and noting Section 1612 of the Manual of Plant Examining Procedure, it is proposed that the title of the invention is *Zoysiagrass* plant named 'BM230'.

BRIEF DESCRIPTIONS OF THE ILLUSTRATIONS

Figure 1:
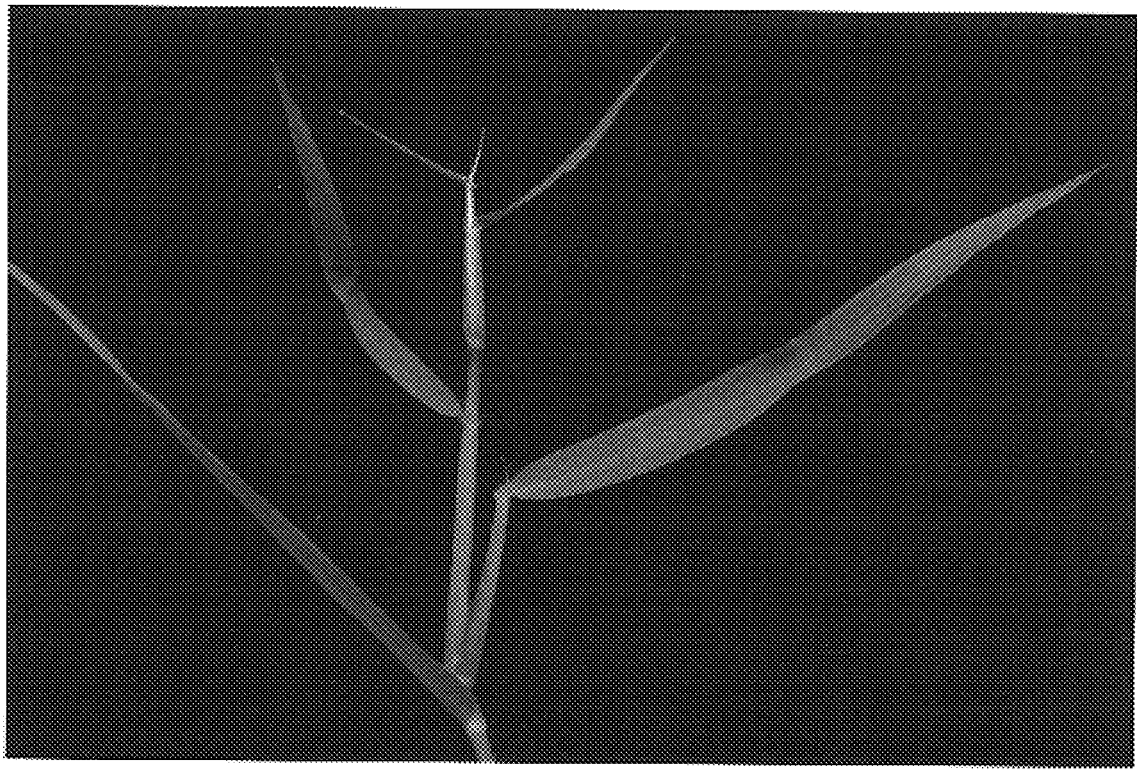

FIG. 1. Tiller of 'BM230' *zoysiagrass*.

Figure 2:
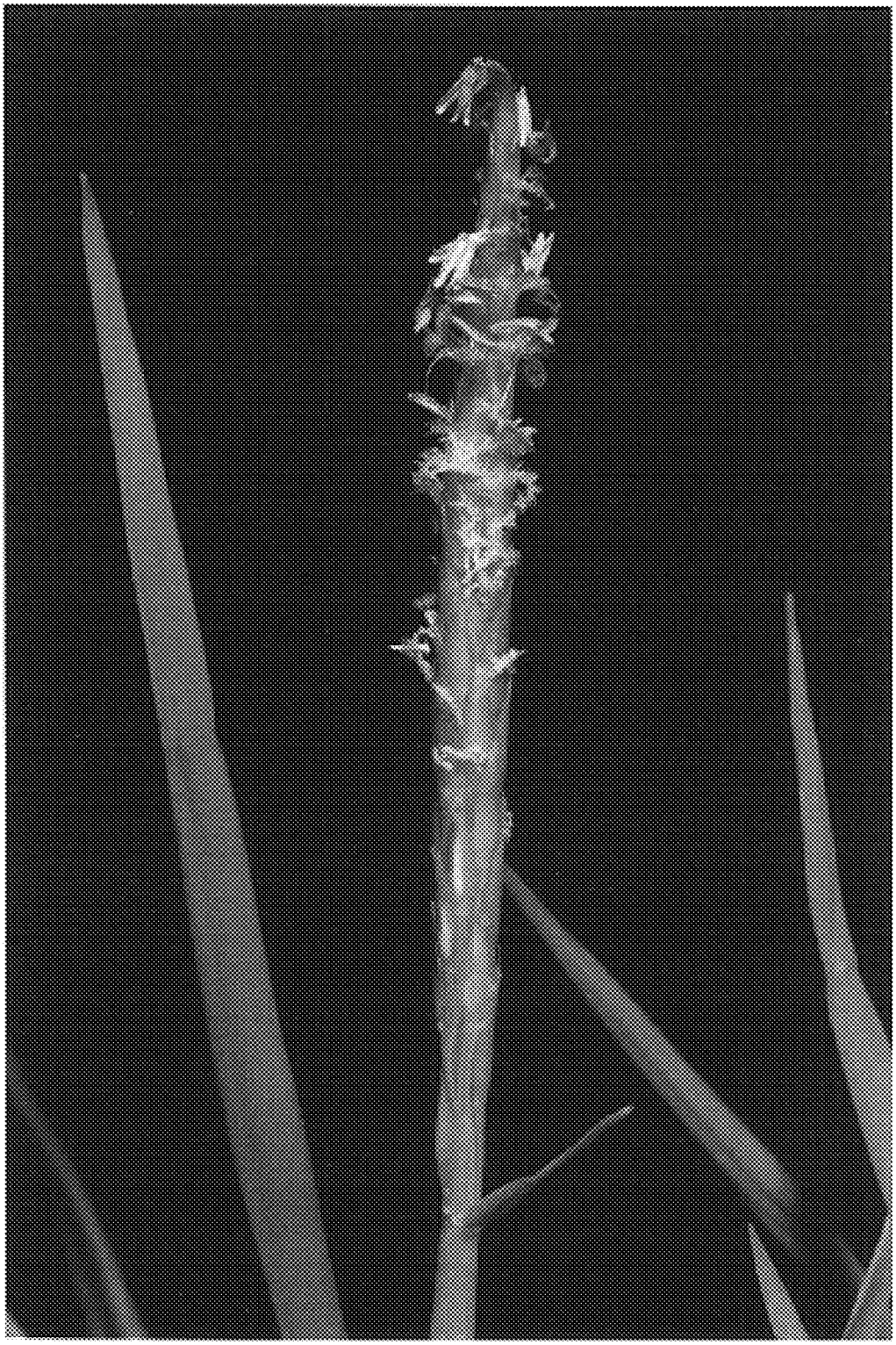

FIG. 2. Inflorescence of 'BM230' *zoysiagrass*.

COMPLETE DESCRIPTION OF THE VARIETY

'BM230' was characterized in greenhouse and field conditions. 'BM230' is a unique variety of *zoysiagrass* (*Zoysia japonica* (L.)) Merr. that was discovered under cultivated conditions in a lawn originally planted with Meyer and Chinese common *zoysiagrass*. 'BM230' was identified in the lawn as having a leaf texture more coarse than its suspected parent 'Meyer'. The lawn was located in USDA Plant Hardiness Zone 7. 'BM230' was propagated by the inventor under field and greenhouse conditions in Parker, Tex. by cutting of rhizomes and stolons, rooting them in soil, and planting of the rooted material to provide planting stock for studying performance and for comparison of morphological characters after propagation. 'BM230' has been propagated by rhizomes, stolons, tillers, and sod. Asexually reproduced plants of 'BM230' have remained stable and true to type through successive generations of propagation. No seedling establishment from 'BM230' has been noticed in either greenhouse or field studies.

'BM230' is a perennial *zoysiagrass* that spreads by both stolons and rhizomes. Characteristics of 'BM230' measured in 2003 were taken from plants that were approximately 15 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'BM230' has a more coarse leaf texture than the suspected parent 'Meyer', and the closest width class cultivars 'Crowne' or 'El Toro' (Table 1) when measured under greenhouse conditions in Lebanon, Oreg., 2003. 'BM230' has a longer floral area than 'Meyer', 'Crowne', and 'El Toro', with shorter anthers than 'Crowne' (Table 2). 'BM230' has no adaxial surface leaf hairs compared to the varieties 'Meyer' and 'Cavalier' that have leaf hairs present (Table 3). No seeds of 'BM230' have developed; no seedlings have been noted in field production area or field test areas. The inflorescences produced in the greenhouse have consisted of empty glumes. 'BM230' has shown susceptibility to the zoysiagrass mite when tested at 17 sites across the US in the 2002 National Turfgrass Evaluation Program (NTEP)—2004 (Table 4). In the NTEP–2004, 'BM230' had intermediate resistance to *zoysia* patch, was susceptible to cool-season brown patch, and had good resistance to dollar spot (Table 4). 'BM230' shows turf density similar to 'Meyer'. 'BM230' has shown good turfgrass performance and temperature adaptation when tested as far north as Dallas, Tex., USDA hardiness zone 7b, which would extend the area of adaptation for 'BM230' in a line from central Georgia across nothern Arkansas through Central to North Texas in an East/West line and on a North/South line from central Georgia south through Mexico. 'BM230' will be limited only by winter survival in colder regions. 'BM230' is similar to most medium to coarse textured zoysiagrasses in water use demands as shown in test situations near Dallas, Tex., and will be limited by adequate precipitation in drier to arid regions. 'BM230' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2003.

| Variety | Length, 3rd youngest crown leaf --cm-- | Width, 3rd youngest crown leaf --mm-- | Leaf Texture Class |
|---|---|---|---|
| 'BM230' | 5.03 | 4.25 | Coarse |
| 'Cashmere' | 3.68 | 1.89 | Fine |
| 'Diamond' | 2.02 | 1.13 | Very Fine |
| 'Emerald' | 4.85 | 2.10 | Fine |
| 'Royal' | 1.92 | 1.63 | Very Fine |
| 'Cavalier' | 2.15 | 1.87 | Very Fine |
| 'Meyer' | 6.47 | 3.64 | Medium-Coarse |
| 'Crowne' | 5.40 | 3.85 | Medium-Coarse |
| 'El Toro' | 3.80 | 3.32 | Medium-Coarse |
| t, p = 0.05 | 2.370 | 0.150 | |

TABLE 2

Inflorescence and leaf characters of selected zoysiagrass cultivars, measured under greenhouse conditions in Lebanon, OR, 2003.

| Variety | Length floral area --cm-- | Length, flag leaf collar to first lower node --mm-- | Sheath length, crown leaf --cm-- | Anther length --mm-- | Node width at base of inflorescence --m-- |
|---|---|---|---|---|---|
| 'BM230' | 4.73 | 5.83 | 2.1 | 2.55 | 1.29 |
| 'Emerald' | 1.44 | 4.15 | 1.81 | 1.29 | 0.76 |
| 'Cashmere' | 1.76 | 13.48 | 1.40 | 1.31 | 0.60 |
| 'Meyer' | 3.10 | 3.78 | 1.80 | 2.17 | 0.78 |
| 'Crowne' | 3.16 | 9.00 | 1.74 | 3.50 | 0.72 |
| 'El Toro' | 3.78 | 8.38 | 1.53 | 1.50 | 0.99 |
| t, p = 0.05 | 0.128 | 2.710 | 0.131 | 0.010 | 0.013 |

TABLE 3

Adaxial leaf hair length measurements of selected zoysiagrass cultivars, measured under greenhouse conditions in Lebanon, OR, 2003

| Variety | Hair length, adaxial leaf --mm-- |
|---|---|
| 'BM230' | 0.00 |
| 'Emerald' | 2.153 |
| 'Cashmere' | 0.000 |
| 'Meyer' | 1.767 |
| 'Royal' | 0.000 |
| 'Crowne' | 1.247 |
| 'Cavalier' | 2.029 |
| 'El Toro' | 1.263 |
| t, p = 0.05 | 0.080 |

TABLE 4

Disease and insect response of selected zoysiagrass cultivars, measured in the 2002 National Turfgrass Evaluation Program for year 2004.

| Variety | Zoysia Patch[1] | Cool-season Brown Patch[1] | Dollar Spot[1] | Zoysiagrass Mite[2] |
|---|---|---|---|---|
| 'BM230' | 7 | 1.3 | 8.3 | 2 |
| 'Emerald' | 9 | 1.3 | 8 | 9 |
| 'Zorro' | 9 | 1.3 | 8 | 9 |
| 'Meyer' | 9 | 2.3 | 8 | 8.7 |
| Chinese Common | 5 | 4.7 | 8.3 | 7 |
| 'Himeno' | 4.7 | 1.7 | 8.3 | 1.7 |
| GN-Z | — | — | 7.7 | 9 |
| LSD, 0.05 | 3.5 | 2.8 | 1.2 | 1.3 |

[1]Rated 1–9, 9 = no disease
[2]Rated 1–9, 9 = no damage

COMPLETE BOTANICAL DESCRIPTION OF THE VARIETY

Origin: 'BM230' is a cultivar of a single clone discovered under cultivated conditions in a Parker, Tex. lawn of 'Meyer' and Chinese common *zoysiagrass*.

Classification: *Zoysia japonica* (L.) Merr.

Growth habit: 'BM230' is a perennial plant that spreads by stolons and rhizomes and produces a dense, coarse textured turfgrass. The inflorescence of 'BM230' is a terminal spike-like raceme, with spikelets on short pedicels.

Leaf blade: Rolled in the bud, concave surface.

Leaf blade pubescence: Sparse hairs on edge of leaves only, 2.0 mm.

Leaf sheath pubescence: Few long hairs at mouth of sheath, mean length: 4.18 mm.

Leaf blade margin: Rough.

Leaf blade veins: Obscure.

Leaf blade flexibility (softness): Medium soft.

Vegetative leaf, third youngest vegetative leaf:

*Blade length range.*—2.1 cm to 9.3 cm, mean length: 5.03 cm.

*Blade width mean.*—4.25 mm.

*Sheath length mean.*—2.06 cm.

Stolon leaf angle, third youngest leaf: 82.3 (Meyer: 98.1; El Toro: 100.6).

Inflorescence characters:

*Culm total length, including floral area to node below flag leaf.*—12.9 cm. Length of stem of inflorescence: 8.0 cm. Floral area length: 4.8 cm.

*Culm width, stem thickness, base of floral area.*—1.29 mm.
*Anther length.*—2.55 mm.
*Floret (seed) length.*—5.18 mm.
*Floret (seed) width.*—1.21 mm.
*Node thickness, node below flag leaf.*—1.8 mm.
*Pedicel length.*—3.18 mm.
*Flag leaf length.*—1.33 cm.
*Flag leaf width.*—2.38 mm.

Mature plant height, including inflorescence: BM230: 20.2; Marion: 18.8 cm; Meyer: 15.0 cm.

Color notations, vegetative characters, based on The R.H.S. Colour Chart (light quality, photoperiod, and general growth of the plants affect color notations):
*Leaf blade color adaxial leaf surface.*—137A green.
*Leaf blade color abaxial leaf surface.*—137A green.
*Stolon colon.*—59A red purple and 146D yellow green.

Color notations, floral characters, based on The R.H.S. Colour Chart (light quality, photoperiod, and general growth of the plants affect color notations):
*Culm stalk.*—146D yellow green.
*Stigma.*—155D white.
*Anthers, mature, dried.*—158A yellow white.

Turf quality (rated 1–9, 9 best): 4; 'Meyer': 5; 'El Toro': 4.5.

Turf color (rated 1–9, 9 best): 6; 'Meyer': 5; 'El Toro': 4.

Turf density establishment rating (rated 1–9, 9 best): 5.5; 'Meyer': 4; 'El Toro': 4.

Leaf texture rating (rated 1–9, 9 best): 3; 'Meyer': 4; 'Diamond': 9.

Disease susceptibility (rated 1–9, 9=no disease):
*Dollar spot.*—'BM230': 8.3; 'Meyer': 8; 'Emerald': 8; 'GN-Z': 7.7.
*Brown patch (cool-season).*—'BM230': 1.3; 'Meyer': 2.3; 'GN-Z': 1.0.
*Zoysia patch.*—'BM230': 7; 'Meyer': 9.0; 'Chinese Common': 5.0.

*Zoysiagrass* mite susceptibility (rated 1–9, 9=no damage): BM230: 2; 'Meyer': 8.7; 'Emerald': 9.

References Cited

U.S. Patent Documents

October, 1998. Engelke, M. C. U.S. Plant Pat. No. 10,636. 'Diamond' *zoysiagrass*

October, 2000. Engelke, M. C. U.S. Plant Pat. No. 11,570. 'Crowne' *zoysiagrass*

December, 1986. Youngner, V. B. U.S. Plant Pat. No. 5,845. 'El Toro' *zoysiagrass*

September, 2000. Engelke, M. C. U.S. Plant Pat. No. 11,515. 'Palisades' *zoysiagrass*

I claim:

1. A new and distinct variety of *zoysiagrass* plant, substantially as described and illustrated herein, characterized particularly by a unique combination of morphological characters.

* * * * *